US012721654B2

(12) United States Patent
Griffith et al.

(10) Patent No.: US 12,721,654 B2
(45) Date of Patent: Sep. 1, 2026

(54) METHODS AND DEVICES FOR DISTRACTION OF HUMAN JOINTS

(71) Applicant: The Chinese University of Hong Kong, Shatin (CN)

(72) Inventors: James Griffith, Sai Kung (CN); Ka Wai David Yeung, Tai Po (CN)

(73) Assignee: The Chinese University of Hong Kong, Shatin (CN)

( * ) Notice: Subject to any disclaimer, the term of this patent is extended or adjusted under 35 U.S.C. 154(b) by 20 days.

(21) Appl. No.: 18/438,172

(22) Filed: Feb. 9, 2024

(65) Prior Publication Data

US 2024/0268865 A1 Aug. 15, 2024

Related U.S. Application Data

(60) Provisional application No. 63/445,208, filed on Feb. 13, 2023.

(51) Int. Cl.

| | |
|---|---|
| ***A61B 17/66*** | (2006.01) |
| *A61B 17/00* | (2006.01) |
| *A61B 17/56* | (2006.01) |

(52) U.S. Cl.
CPC .... *A61B 17/66* (2013.01); *A61B 2017/00743* (2013.01); *A61B 2017/564* (2013.01)

(58) Field of Classification Search
CPC ................ A61B 17/66; A61B 17/6425; A61B 2017/567; A61B 5/705; A61B 5/6825; A61B 5/6824; A61F 5/048; A61F 5/042; A61F 5/04
See application file for complete search history.

(56) References Cited

U.S. PATENT DOCUMENTS 1,389,741 A * 9/1921 Lambert ............. A61F 5/05866 602/21
2,584,203 A * 2/1952 Hart .......................... A61F 5/04 24/129 D
3,087,489 A * 4/1963 Herbert ..................... A61F 5/04 602/33

(Continued)

FOREIGN PATENT DOCUMENTS

CN 114073613 A * 2/2022
WO WO-2021006971 A1 * 1/2021 ........... A61B 17/025

*Primary Examiner* — Jacqueline T Johanas

(74) *Attorney, Agent, or Firm* — Kilpatrick Townsend & Stockton LLP

(57) ABSTRACT

A joint distraction device that is wearable by a patient and user-friendly and associated methods of joint distraction. Such devices can include first and second anchors that secure portions of the patient's body proximal and distal of the joint, the anchors each being attached to a beam and a distance between first and second anchors being adjustable so as to hold the joint being investigated in distraction. For distraction of a wrist joint, the first anchor can be a finger clamp and the second anchor can be an arm sleeve. The finger clamp can include multiple finger traps. The distance between anchors can be adjusted by an adjuster, by extending the beam or by moving an anchor incrementally along the beam. Advantageously, the device is fully wearable by the patient without being attached to external components, thereby improving patient comfort, portability and ease of use.

29 Claims, 8 Drawing Sheets

(56) References Cited

U.S. PATENT DOCUMENTS

| | | | | | |
|---|---|---|---|---|---|
| 3,662,750 | A * | 5/1972 | Jorgensen | A61F 5/04 | 602/35 |
| 3,850,166 | A * | 11/1974 | Tamny | A61F 5/04 | 602/40 |
| 3,872,861 | A * | 3/1975 | Tamny | A61F 5/04 | 602/36 |
| 4,643,177 | A * | 2/1987 | Sheppard | A61F 5/04 | 606/55 |
| 4,945,902 | A * | 8/1990 | Dorer | A63B 21/4025 | 601/40 |
| 5,020,524 | A * | 6/1991 | Donohue | A61F 5/0118 | 602/22 |
| 5,643,186 | A * | 7/1997 | Chinchalkar | A61F 5/0118 | 601/40 |
| 5,702,355 | A * | 12/1997 | Repice | A61F 5/0118 | 602/5 |
| 5,735,806 | A * | 4/1998 | Leibovic | A61F 5/04 | 24/115 M |
| 5,876,363 | A * | 3/1999 | Marx | A61F 5/0118 | 601/40 |
| 5,947,915 | A * | 9/1999 | Thibodo, Jr. | A61F 5/05875 | 602/5 |
| 6,123,704 | A * | 9/2000 | Hajianpour | A61F 5/04 | 606/54 |
| 6,530,893 | B1 * | 3/2003 | Castelli | A61F 5/0118 | 602/32 |
| 7,131,955 | B2 * | 11/2006 | Price | A61F 5/3761 | 602/20 |
| 8,540,656 | B1 * | 9/2013 | Powlan | A61F 5/3761 | 602/32 |
| 11,771,581 | B1 * | 10/2023 | Mansuripur | A61F 5/048 | 602/22 |
| 11,857,447 | B1 * | 1/2024 | MacArthur | A61F 5/0118 | |
| 2001/0031937 | A1 * | 10/2001 | Repice | A61F 5/0111 | 602/32 |
| 2002/0169447 | A1 * | 11/2002 | Agee | A61B 17/6425 | 606/60 |
| 2003/0220595 | A1 * | 11/2003 | Lambert | A61F 5/3761 | 602/36 |
| 2005/0240136 | A1 * | 10/2005 | Price | A61F 5/04 | 602/32 |
| 2006/0200061 | A1 * | 9/2006 | Warkentine | A61F 5/04 | 602/32 |
| 2007/0167893 | A1 * | 7/2007 | Frisbie | A61F 5/0113 | 602/12 |
| 2009/0030353 | A1 * | 1/2009 | Bonutti | A61H 1/0274 | 601/5 |
| 2010/0069810 | A1 * | 3/2010 | Tanaka | A61F 5/042 | 602/32 |
| 2011/0178449 | A1 * | 7/2011 | Foote | A61F 5/05858 | 602/36 |
| 2012/0046583 | A1 * | 2/2012 | Nakamitsu | A61F 5/05866 | 602/20 |
| 2012/0253410 | A1 * | 10/2012 | Taylor | A61B 17/6458 | 606/86 R |
| 2013/0178777 | A1 * | 7/2013 | DiLorenzo | A61F 5/048 | 602/36 |
| 2015/0088045 | A1 * | 3/2015 | Laurensse | A61F 5/05875 | 602/20 |
| 2016/0136030 | A1 * | 5/2016 | Silva | A61F 5/10 | 601/27 |
| 2018/0168842 | A1 * | 6/2018 | Hunter, Jr. | A61G 13/101 | |
| 2022/0008238 | A1 * | 1/2022 | Wang | A61H 1/0285 | |
| 2022/0117824 | A1 * | 4/2022 | Wang | A61H 1/0288 | |
| 2022/0296403 | A1 * | 9/2022 | Stefansson | A61F 5/048 | |
| 2022/0354683 | A1 * | 11/2022 | Alfonso | A61G 13/124 | |

* cited by examiner

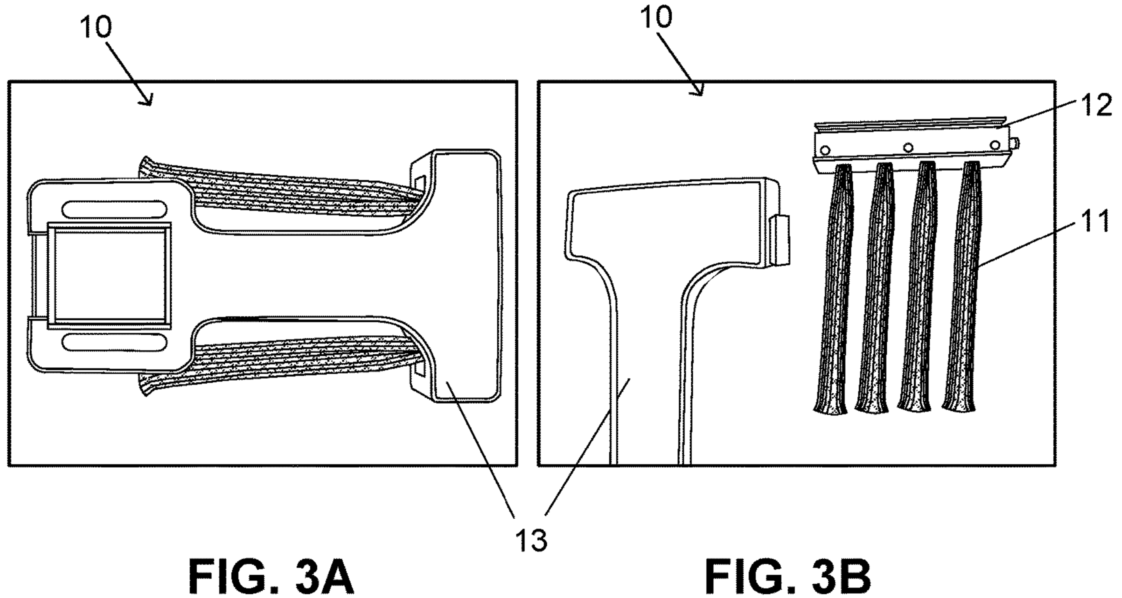
FIG. 3A
FIG. 3B
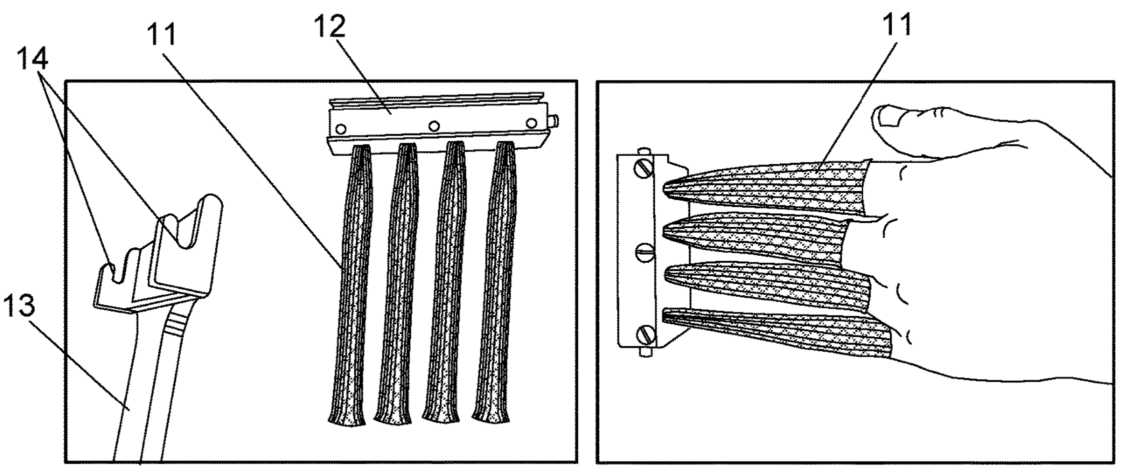
FIG. 3C
FIG. 3D

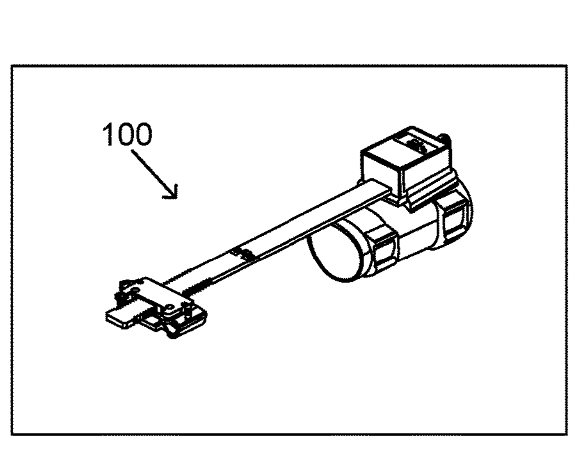
FIG. 6A
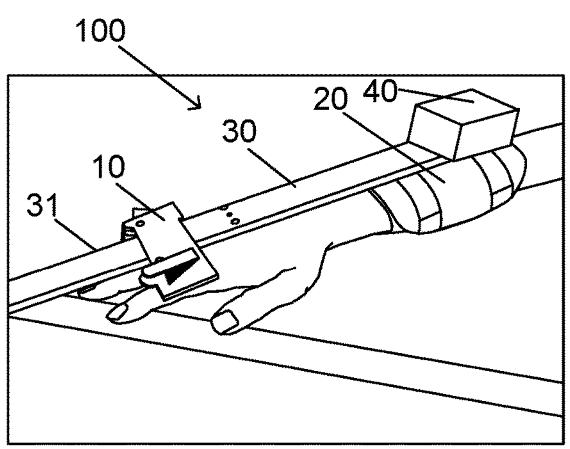
FIG. 6B
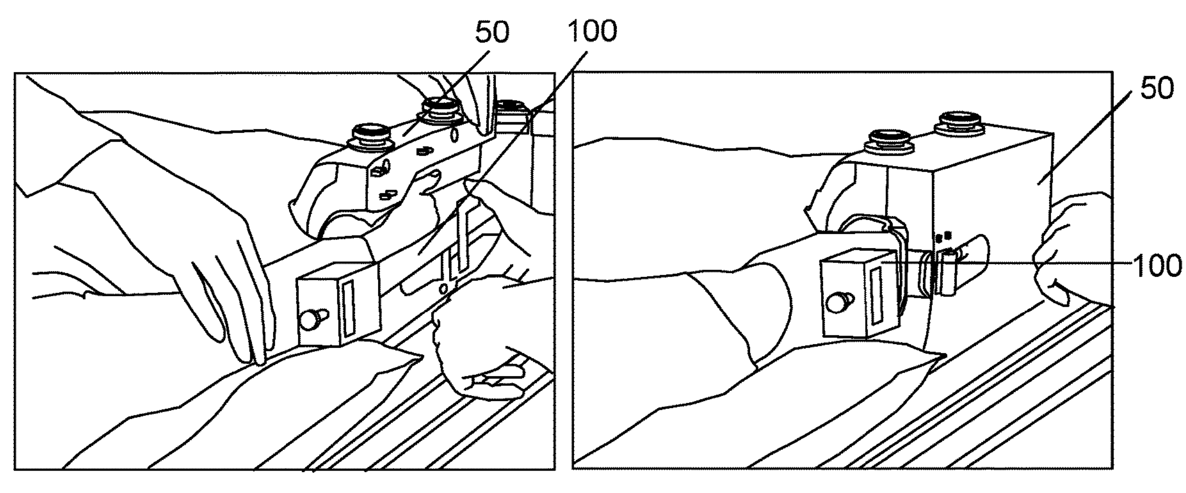
FIG. 6C
FIG. 6D
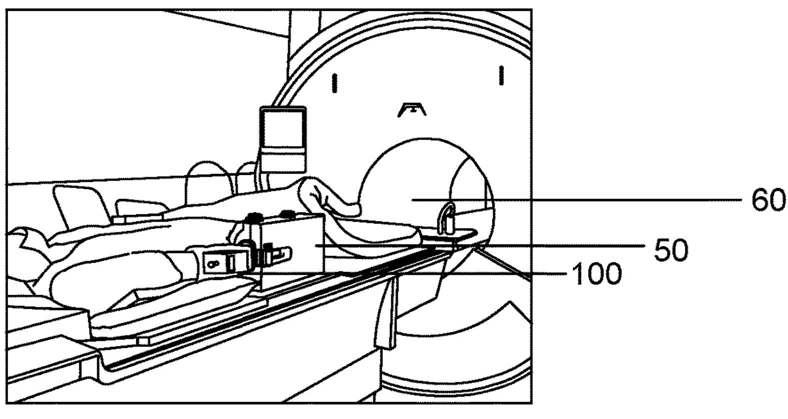
FIG. 6E

METHODS AND DEVICES FOR DISTRACTION OF HUMAN JOINTS

CROSS-REFERENCES TO RELATED APPLICATIONS

This application is a Non-Provisional of and claims the benefit of priority to U.S. Provisional Application No. 63/445,208 filed Feb. 13, 2023, which is incorporated herein by reference in its entirety.

BACKGROUND OF THE INVENTION

The present invention relates generally to distraction of human joints for imaging and/or arthroscopy.

Imaging and arthroscopy of a human joint greatly benefits from distraction (e.g. gapping or separation) of a joint so that the articular cartilage surfaces of the joint can be better visualized or accessed during an imaging or arthroscopic procedure. However, current approaches of joint distraction typically employ fairly cumbersome systems that are connected to pulley and cable systems and weights. Such systems are difficult and time-consuming to position and difficult or impractical to adjust for each patient's needs. Further, these systems often apply forces to other joints not being investigated which poses risks or at least discomfort to the patient. Additionally, such systems are bulky and involve connections to various external components that apply distraction forces, which can interfere with positioning of the patient and accessing the patient during imaging and arthroscopy procedures.

Accordingly, there exists a need for joint distraction methods and systems that can provide suitable distraction of the joint that avoids the difficulties noted above. It would be further advantageous if such methods and systems were less complex, more portable, more comfortable for the patient and user-friendly for the clinician.

SUMMARY OF THE INVENTION

In one aspect, the invention pertains to distraction of peripheral joints to facilitate imaging and/or arthroscopy of the joints.

In one aspect, the invention pertains to a device for distraction of a patient's joint. The device can include a first anchor configured to securely couple to a portion of a patient's body distal of the joint; a second anchor configured to securely couple to a portion of the patient's body proximal of the joint; a beam or bar extending lengthwise between the first and second anchors; and an adjuster configured to adjust a distance between the first and second anchor so as to control distraction of the joint. Preferably, the device is a wearable device, which considerably improves ease of use and patient comfort. In some embodiments, the device is configured for distraction of the wrist joint, the first anchor being configured for coupling to a hand of the patient and the second anchor being configured for coupling to an arm of the patient. In such embodiments, the first anchor can be a finger clamp. In some embodiments, the finger clamp includes multiple finger traps. The finger traps extend toward the patient's fingers from a cross-bar of the first anchor when the device is worn by the patient. The cross-bar can be mated with a base that couples to a distal portion of the beam extending lengthwise between the first and second anchors. The second anchor can include a sleeve with one or more fasteners for securing to an arm of the patient, typically along the forearm. The one or more fasteners can include one or more Velcro tabs for ease of use.

In some embodiments, the first anchor is fixedly secured to the beam and the beam is extendable to adjust the distance between the first and second anchors. In some embodiments, the position of the first and/or second anchor on the beam is adjustable. For example, the beam can include a fluted or keyed portion having ridges or notches by which the beam is extended or by which the first anchor is advanced by actuation of the adjuster to incrementally adjust a position of the first anchor thereby adjusting the distance between the first and second anchors to control distraction forces on the joint.

In some embodiments, the device is formed of materials that are compatible with MRI imaging of the joint. Preferably, the device is fully wearable and portable. The device can be operable without requiring attachment to any external pulley system, weights or external device or system, which greatly improves portability, comfort, and ease of use.

In some embodiments, the adjuster is manually operated, whereas in other embodiments, the adjuster can be electrically actuated. In some embodiments, the adjuster is automatically operated based on a detected application of force by the device.

In another aspect, the invention pertains to methods of distracting a joint of a patient. Such methods can include steps of: securing a first anchor of a joint distraction device to a first portion of the patient distal of the joint; securing a second anchor of the device to a second portion of the patient proximal of the joint, the first and second anchor being connected by a beam extending length-wise therebetween; and adjusting, with an adjuster of the device that is operably coupled to the beam, a distance between the first and second anchor, thereby placing the joint under sufficient tension for distraction of the joint. Preferably, the joint distraction device is wearable by the patient such that the method further includes performing imaging and/or arthroscopy of the joint while the joint distraction device is worn by the patient. For distraction of the wrist joint, the first anchor can be a finger clamp and the second anchor can be an arm sleeve. In some embodiments, the finger clamp includes multiple finger traps.

In some embodiments, adjusting the distance between the first and second anchor includes extending the beam from one of the first and second anchors. In other embodiments, the adjusting the distance includes adjusting a position of one of the first and second anchors on the beam. In such embodiments, adjusting the distance between the first and second anchor can include incrementally adjusting the position of the first anchor on a plurality of notches or ridges on a fluted or keyed portion of the beam.

A further understanding of the nature and advantages of the present invention may be realized by reference to the remaining portions of the specification and the drawings.

BRIEF DESCRIPTION OF THE DRAWINGS

FIGS. 3A-3D show views of a first anchor design having finger traps, in accordance with some embodiments.

FIGS. 6A-6B shows the joint distraction device of FIG. 1 before and after being positioned on a patient to distract the wrist joint, in accordance with some embodiments.

FIGS. 6C-6E shows subsequent imaging of the wrist joint while the device is worn by the patient, in accordance with some embodiments.

DETAILED DESCRIPTION

Figure 1:
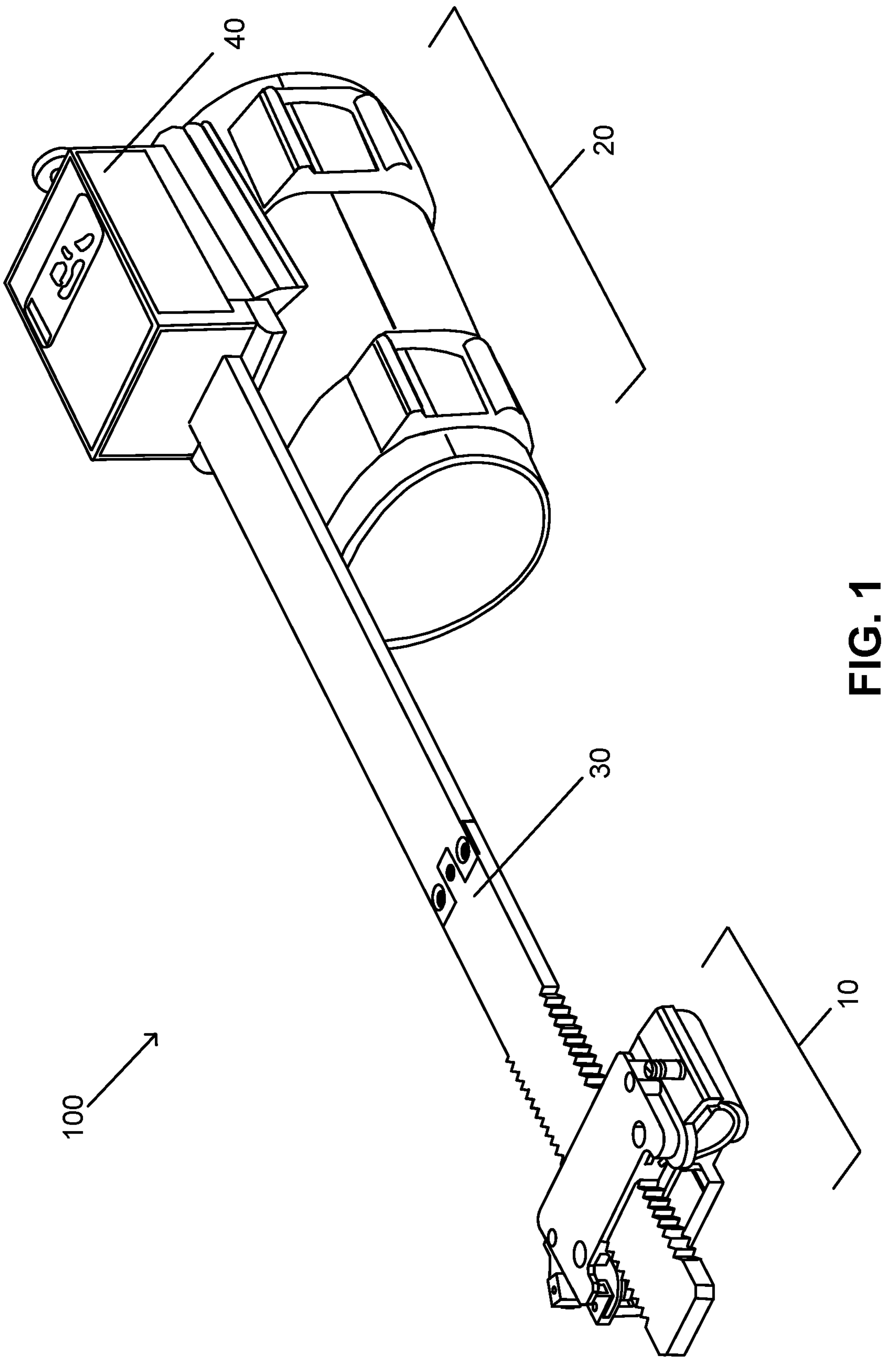
FIG. 1 shows a joint distraction device for distraction of the wrist joint, in accordance with some embodiments.

The invention relates to methods and devices for distraction of joints in a human patient. Preferably, the device is a readily attachable distraction device that will enable controlled distraction of peripheral joints for medical purposes.

Distraction of joints (e.g. gapping or separation) is used for imaging or arthroscopy in human patients. In some joint areas, the articular cartilage is normally closely opposed. This is particularly the case in the thumb, wrist, elbow, shoulder, hip, and ankle joints. This close opposition of the articular cartilage surfaces of the joints impairs complete visualization of the articular cartilage surface. Therefore, distraction of joints is necessary to see and, if necessary, treat articular cartilage surface injury more clearly. Such joint distraction can be undertaken during both of an imaging procedure, such as magnetic resonance imaging (MRI) examination, and arthroscopy to improve visibility of the articular cartilage surface.

In one aspect, the present invention provides a simple, externally attached device that uses two securely attached anchors on either side of the joint under investigation and a straightforward adjustment mechanism to increase distance between the anchors in a gradated controlled manner. For distraction of the wrist joint, for example, a first anchor can be placed on the hand, in particular, the four fingers (excluding the thumb) and a second anchor can be placed on a mid-forearm respectively. The adjustment mechanisms can be a length-adjustable slide connecting the two anchors, which is used to create a separation force between the fingers and forearm, thus distending the intervening wrist joint. It is appreciated that this same general concept can be applied to various other joints, such as any of the joints of the thumb, fingers, wrist, elbow, shoulder, hip, knee, and ankle.

The presently described device and methods provide marked advantages and improvements over existing approaches. Current methods to distract peripheral joints typically involve: (a) arthrography or (b) application of peripheral traction force. Arthrography involves injection of dilute contrast into the joint to distend the intraarticular space during imaging investigations. This procedure causes some patient discomfort, is time consuming, minimally invasive, and preferentially distends the anatomical joint recesses rather than distracting the articular cartilage surfaces. Application of a peripheral traction force physically distracts the joint. Such traction forces can be applied during either arthroscopy or imaging investigations. For example, to distract the wrist joint during MR imaging or wrist arthroscopy, finger traps with weights (e.g. sandbag weights) attached to a nonelastic rope and pulley system are used to pull on the fingers which in turn separates the bones located on either side of the wrist. Similarly, using weights to pull the foot away from the leg is currently used to distract the ankle or hip joints to improve the cartilage surface visibility. However, this approach of attaching external weights to the limbs is cumbersome and has various disadvantages. For example, during MRI traction of the wrist, the patient must lie in an uncomfortable prone position with the hand above the head to enable traction using a rope and pully system outside the bore of the MR system. It is impractical to adjust the sandbag weights to the correct traction force for each patient. Also, joint traction as currently applied is nonselective as, for example, traction applied to distend the wrist joint will also inadvertently distend the elbow and shoulder joint potentially aggravating other joints, causing patient discomfort and posing risk to the patient.

Advantageously, the present invention overcomes the many disadvantages of existing joint distraction methods. The presently described device provides any of the following benefits: (a) noninvasive, (b) versatile, (c) faster than application of traction, (d) more selective in that only the main joint under investigation is mainly distracted, (e) readily adjustable, and (f) more comfortable than current methods of joint distraction.

As noted above, some parts of human joint spaces are very closely opposed and a method to improve the visibility of articular cartilage during investigation of these joints with either imaging studies or arthroscopy is desirable. Preferably, the method should be easy to use, be wearable, compact enough to fit into existing systems with no complicated rope, pulley and weights system, and provide a readily adjustable force of joint distraction. By employing the advantageous approach described herein, the present invention provides a user friendly wearable device that dependably and reliably provides sufficient joint distraction to improve visibility of opposing articular surfaces of joints during MRI examination or an arthroscopy procedure.

A detailed technical description of the invention as applied to the imaging of the wrist joints is presented in FIG. 1 as an example by which to illustrate the key concepts of this invention. It is appreciated that a similar concept can be applied to other peripheral joints. To distract the wrist joint, anchors on four fingers (omitting the thumb) and the mid-forearm are applied. The force necessary to distract the distance between the two anchors is provided by means of a rigid and lengthwise adjustable slide beam.

FIG. 1 shows an exemplary embodiment of a joint distraction device 100. Device 100 includes a distal anchor 10 for anchoring to a portion of the body distal of the joint, a proximal anchor 20 configured for anchoring to a portion of the body proximal of the joint and a beam 30 extending between the proximal and distal anchoring portion. Device 100 further includes adjuster 40 that changes a distance between the anchors so as to apply a distending force between the proximal and distal anchor points. Adjuster 40 can be configured as a movable member or mechanism and can be manually or electrically actuated.

Figure 2A:
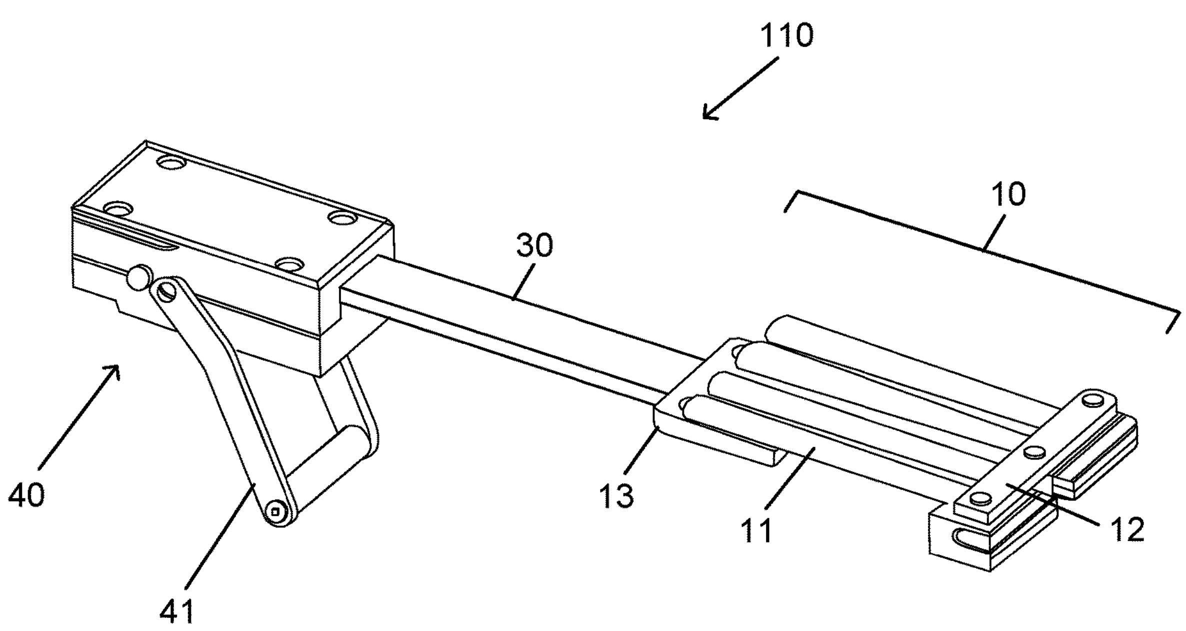
FIGS. 2A-2B show views of an alternative design of a joint distraction device for distraction of the wrist joint, in accordance with some embodiments.
Figures 4A, 4B:
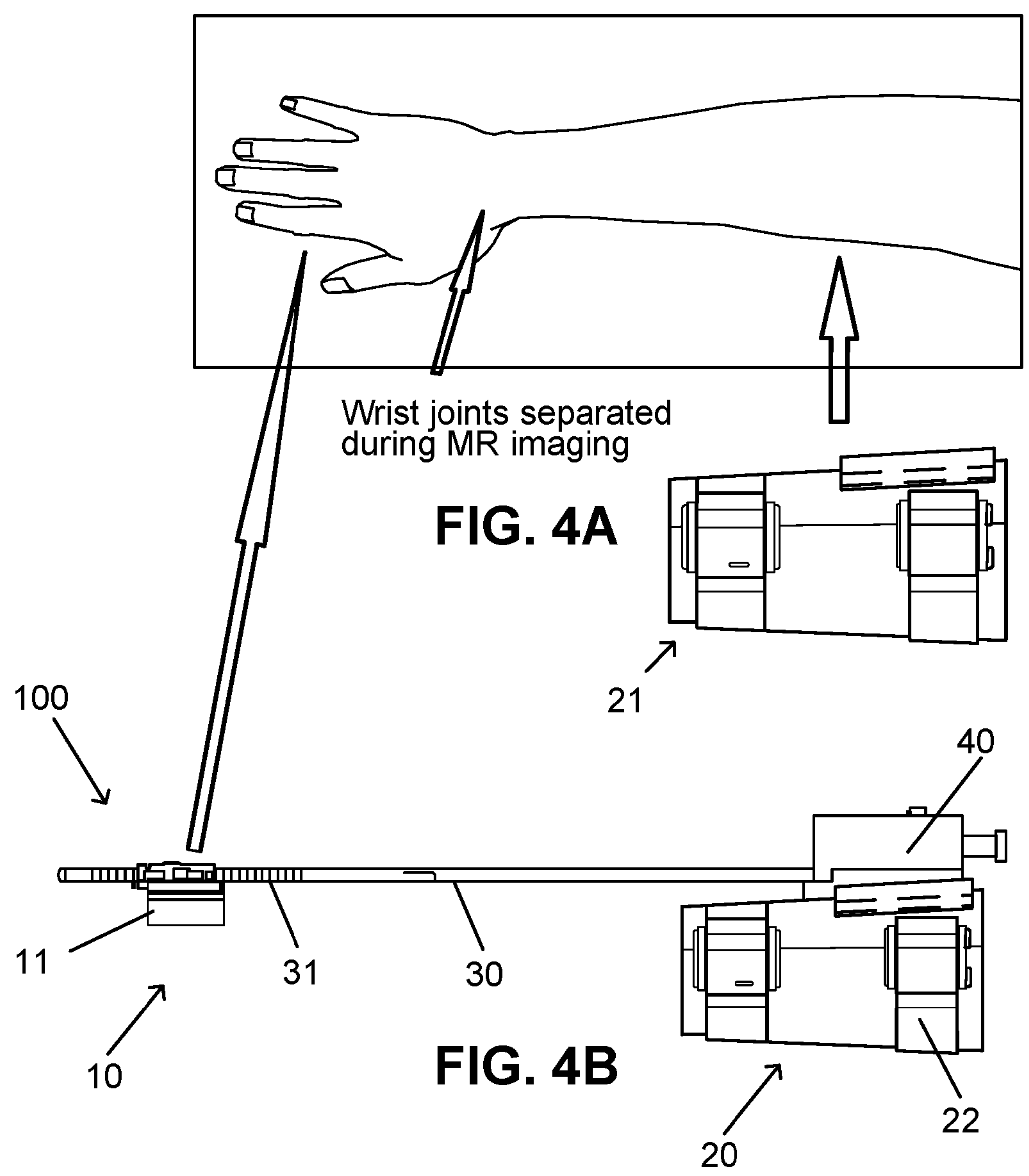
FIGS. 4A-4B shows the joint distraction device of FIG. 1 relative a patient's arm, in accordance with some embodiments.

Device 100 in FIG. 1 is configured for distraction of the wrist joint such that the distal anchor 10 is configured for coupling with the hand distal of the wrist and the proximal anchor 20 is configured for coupling with the arm proximal of the wrist. By this approach, the device distracts the wrist joint without distending or straining the elbow or shoulder joints. As shown, the distal anchor 10 is configured with a finger clamp to couple with one or more fingers of the hand. In some embodiments, the finger anchor point can be provided by four plastic 'finger traps' which comprise a cylindrical, helically wound plastic braid which comfortably trap the fingers. The alternative design of a finger clamp using "finger traps" is shown in FIGS. 2A and 3A-3B. The second anchor point can be provided by a sleeve that tightly conforms to the contour of the forearm. Additional details of this sleeve example are shown in FIGS. 4A-4B.

Figure 2B:
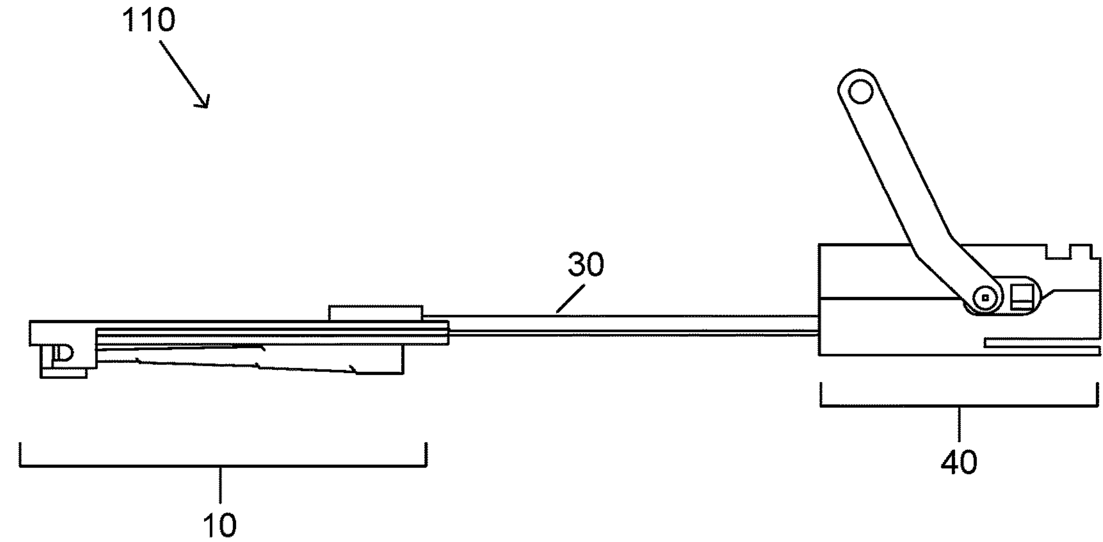

FIGS. 2A and 2B show a perspective view and side view of an assembled joint distraction device 110 (second anchor not shown). This device utilizes a finger clamp 11 that is defined by four finger traps. The finger traps are connected to a cross-bar 12 that is mated to a T-shaped base 13 that is coupled to the beam 30 extending from the adjuster 40. In this embodiment, the adjuster 40 has a press-to-lock mechanism with a lever 41 that can be pulled proximally to retract the extendable beam to apply force to the finger traps, thereby creating the force necessary to couple the fingers to facilitate distention of the wrist joint.

FIGS. 3A-3D show detail view of an example finger clamp using Chinese "finger traps." The distal tips of the finger traps are attached to a plastic cross-bar which helps to ensure uniform traction to all fingers. FIG. 3A shows the assembled finger clamps 11 comprising the "finger traps" extending from cross-bar 12 coupled to the T-shaped base 13. FIG. 3B shows a disassembled view of these components. As shown, the cross-bar 12 has protruding extensions that mate with the T-shaped receiving end of the base 13. As shown in FIG. 3C, the T-shaped base 13 has two fork-like troughs 14 that receive the protruding extensions from the cross-bar 12. FIG. 3D shows how the "finger traps" securely holding the fingers, creating anchor points for the extendable beam to exert a force sufficient to expand the wrist joint in distraction.

An alternative method to using finger traps is to employ a "finger clamp" with adjustable tightening force, for example, as shown in FIG. 1. In some embodiments, all contact surfaces between the finger clamp and the skin are covered with a non-slip, silicon-like material with protruding humps to allow blood circulation while the fingers are securely clamped. In some embodiments, the top-side of the clamp (same side as the dorsal surface of the fingers) can include a push-and-lock mechanism together with a press-to-release mechanism (same or similar as in FIGS. 2A-2B) that allows the beam to lock in one direction only (i.e. while maintaining a distending force between the two anchor points).

FIGS. 4A-4B show a patient's arm relative a joint distention device. FIG. 4A shows the patient's forearm, hand and the wrist joint to be investigated by MR imaging. FIG. 4B shows a side view of joint distention device 100, which includes a distal anchor 10, which is a finger clamp 11 in this embodiment, and a proximal anchor 20 defined as an arm sleeve that is worn on the patient's forearm. In this embodiment, the proximal anchor 20 is a textile sleeve 21 sized to fit on the patient's forearm with adjustable fasteners 22 (e.g. straps with Velcro magic tapes) to ensure the sleeve wraps around the forearm securely and ensure it does not slip towards the elbow. The human forearm has a greater circumference towards the elbow which prevents the forearm sleeve 21 slipping towards the elbow. Thus, the sleeve 21 with a mechanism to receive the proximal end of the extendable beam forms the proximal anchor 20 of the device. In this embodiment, the slide beam 30 includes a fluted or keyed portion 31 that includes gradated notches or ridges, which facilitate incremental adjustment to control separation between anchors to ensure controlled distraction of the intervening wrist joint. In some embodiments, the adjuster 40 includes an elongate member extending through the beam that allows incremental adjustment of the distal anchor along the graduated notches or ridges. Depending on the individual need of the patient, the distraction device can be applied to the volar or dorsal aspects of the wrist.

Figure 5A:
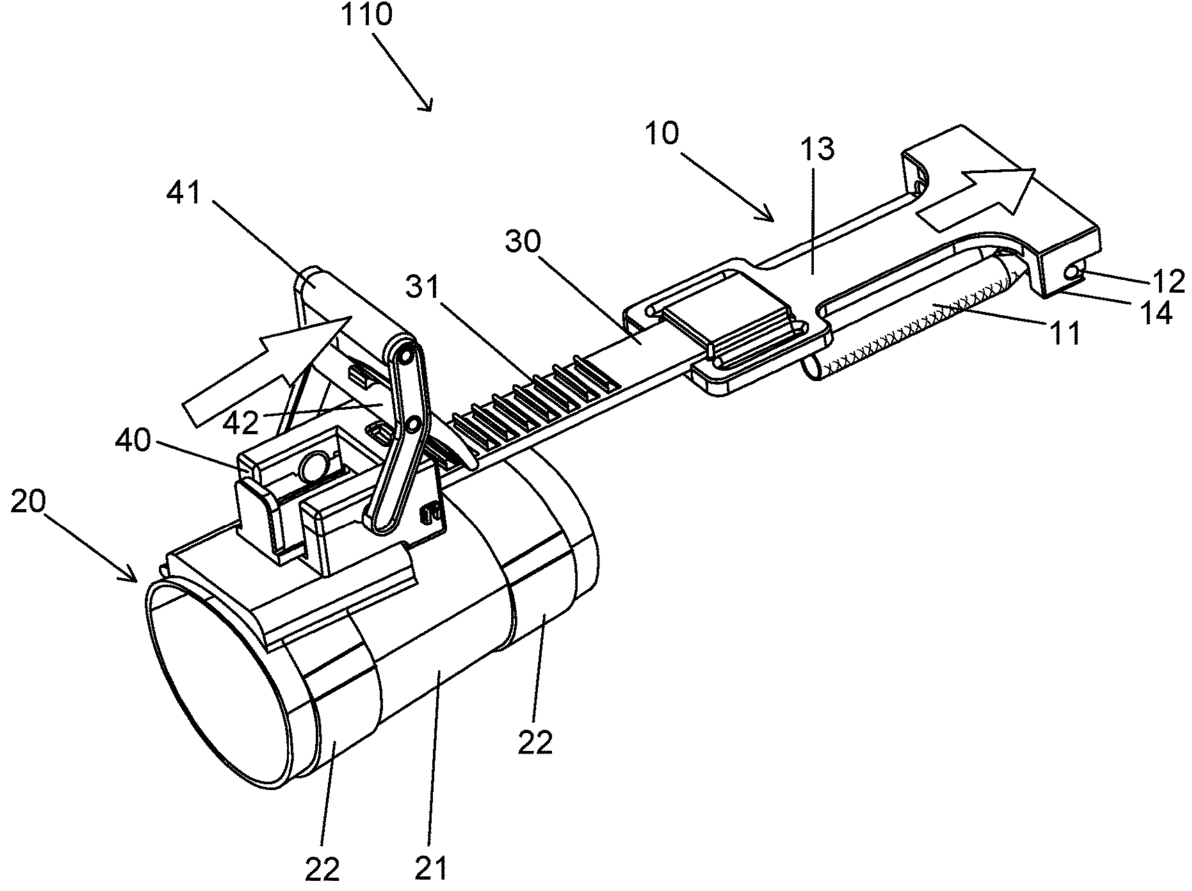
FIGS. 5A-5B shows a joint distraction device, which is consistent with the embodiment of FIG. 2A, before and after extension of the first anchor by actuation of the adjuster to distract the wrist joint, in accordance with some embodiments.
Figure 5B:
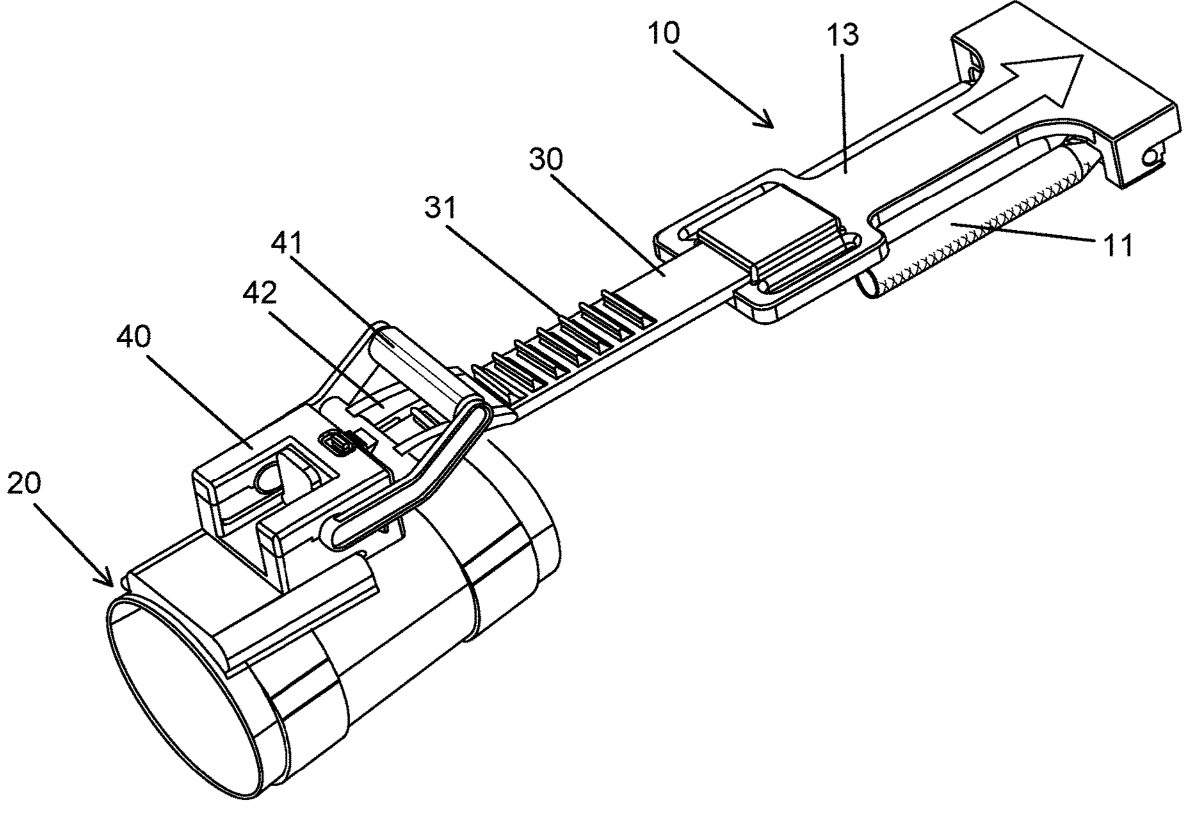

FIGS. 5A-5B show an exemplary joint distraction device 110 consistent with the embodiment of FIG. 2 shown before and after extension of the first anchor 10 from the second anchor 20 to distract the wrist joint when worn by the patient. Device 110 includes the same or similar components as described in previously described embodiments. Device 110 has a second anchor 20 defined as a sleeve with adjustable straps 22 for securing on the patient's forearm and from which beam 30 extends distally to the first anchor 10 having finger traps for attaching to the patient's fingers. As shown in FIG. 5A, adjuster 40 is defined by a mechanism having a rotatably attached lever 41 that when pushed forward, forces a pivotally attached latch 42 to engage ridges or notches of fluted or keyed portion 31 of beam 30 in the forward direction. As shown in FIG. 5B, this forward movement of lever 41 and attached latch 42 distally extends beam 30, increasing a separation distance between the first and second anchors 10, 20 when the first anchor is secured to the patient's fingers while the second anchor 20 is secured to the patient's forearm, thereby distracting the wrist joint. Thus, by this mechanism, the length of the beam may be increased incrementally and by taking into account the patient's tolerance to the force being applied, an optimal joint distension may be achieved.

FIGS. 6A-6D show an exemplary joint distraction device for distention of the wrist joint, the device worn on the user, and subsequent imaging of the wrist joint. FIG. 6A shows the exemplary joint distraction device 100 of FIG. 1, which includes a distal finger clamp as the distal anchor and an arm sleeve as the proximal anchor. FIG. 6B shows the joint distraction device 100 worn by the patient, whose fingers are placed through the finger clamp of the distal anchor 10, the position of which is controlled by adjuster 40 by incremental movement along the notches or ridges of fluted portion 31 of beam 30, while the proximal anchor 20 is secured to the forearm. The device is adjusted by adjuster 40 to separate the anchors until the wrist joint is distracted by the force applied by the proximal and distal anchors. After the wrist joint is satisfactorily distracted for imaging, the patient is then brought inside the MRI scanner. As shown in FIG. 6C, the device is fully wearable by the patient and allows the patient's wrist to be imaged while the patient is in the supine position, which is much more comfortable than conventional approaches of joint distraction. As shown in FIG. 6D, the distended wrist is placed in a wrist RF coil 50 as the signal receiver of the MR scanner. FIG. 6E shows the patient being moved inside the MRI Scanner 60 for imaging of the patient's wrist while the joint is held in distraction by the device 100.

As shown, the device is a wearable, user friendly means to distract peripheral joints. There are currently no such wearable product in the market. As discussed above, clinical centers have to rely on in-house custom made clamps, ropes, weights and a pulley systems. Current methods are too cumbersome and not all centers have the technical expertise to assemble such means to distend joints for imaging or arthroscopy. Further, this device is easily adjustable for each individual patient to ensure proper joint distraction and avoid patient discomfort or risk to other joints.

Figure 7:
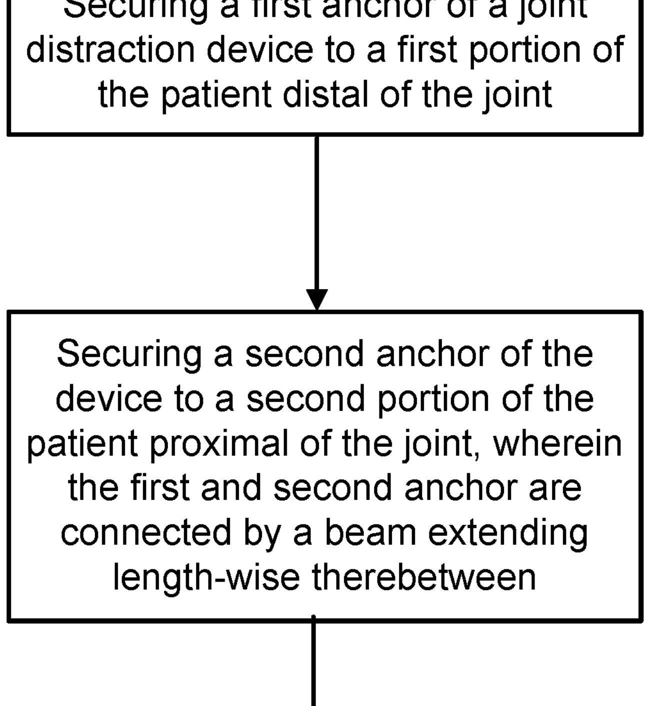
FIG. 7 shows a method of distracting a joint by a joint distraction device, in accordance with some embodiments.

FIG. 7 depicts a method of joint distraction, in accordance with some embodiments. The exemplary method includes steps of: securing a first anchor of a joint distraction device to a first portion of the patient distal of the joint; securing a second anchor of the device to a second portion of the patient proximal of the joint, wherein the first and second anchors are connected by a beam extending length-wise therebetween; and adjusting, with an adjuster operably coupled to the beam, a distance between the first and second anchor, thereby distracting the joint. It is appreciated that this method can be applied to distraction of the wrist joint, as described previously, or can be applied to any joint being investigated.

While the above is a complete description of specific embodiments of the invention, the above description should not be taken as limiting the scope of the invention as defined by the claims. Various features, embodiments and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It is recognized that the terms "comprising," "including," and "having," as used herein, are specifically intended to be read as open-ended terms of art.

What is claimed is:

1. A joint distraction device for distraction of a patient's wrist joint, the device comprising:

a first anchor configured to securely couple to a hand of a patient's body distal of the wrist joint, wherein the first anchor is configured for immobilizing the hand of the patient;

a second anchor configured to securely couple to a portion of the patient's body proximal of the joint, wherein the second anchor is configured for coupling to a forearm of the patient;

a beam extending lengthwise between the first and second anchors, a crossbar of the first anchor securely affixed to the beam at a fixed location so as to securely hold the patient's hand in a fixed position when clamped within the first anchor for MRI imaging; and an adjuster configured to adjust a distance between the first and second anchor so as to control distraction of the joint;

wherein the device is formed of materials that are compatible with MRI imaging;

wherein the second anchor is configured to couple entirely on the forearm and the beam is disposed along an outer side of the hand and arm such that the wrist joint is held in distraction with an inner side of the hand and arm positioned straight alongside the patient in a supine position during MRI imaging.

2. The device of claim 1, wherein the device is a wearable device.

3. The device of claim 2, wherein the adjuster is electrically actuated.

4. The device of claim 3, wherein the adjuster is automatically operated based on a detected application of force by the device.

5. The device of claim 1, wherein the first anchor comprises at least two finger clamps, wherein each of the at least two finger clamps is fixedly secured to the cross-bar.

6. The device of claim 1, wherein the first anchor comprises a plurality of finger traps, wherein each of the plurality of finger traps is fixedly secured to the cross-bar at a fixed position.

7. The device of claim 6, wherein the plurality of finger traps extend toward a patient's fingers from the cross-bar of the first anchor when the device is worn by the patient, wherein the cross-bar is fixedly attached to the beam at the fixed location such that the patient's hand is held in the fixed position for MRI imaging.

8. The device of claim 7, wherein the plurality of finger traps comprise four finger traps that can be advanced toward the hand by pulling of a lever or actuation of the adjuster.

9. The device of claim 7, wherein the cross-bar is mated with a T-shaped base that couples to a distal portion of the beam extending lengthwise between the first and second anchors.

10. The device of claim 1, wherein the beam includes a fluted portion on which the first anchor is moved or by which the beam is extended and the adjuster is configured to incrementally adjust a position of the first anchor via engagement with the fluted portion to adjust the distance between the first and second anchors.

11. The device of claim 1, wherein the second anchor comprises a sleeve with one or more fasteners for securing to the forearm of the patient.

12. The device of claim 11, wherein the one or more fasteners comprise one or more Velcro tabs.

13. The device of claim 1, wherein the device is fully wearable and operable without attachment to any external pulley system.

14. The device of claim 1, wherein the device is fully wearable and operable without attachment to any external weights.

15. The device of claim 1, wherein the device is fully wearable and operable without being attached to any external device or system.

16. The device of claim 1, wherein the adjuster is manually operated.

17. The device of claim 1, wherein the device extends linearly such that the arm is configured to be held straight with both the elbow and wrist joints unbent.

18. The device of claim 1, wherein the device is configured to attach on the outer side of the patient's hand and arm such that the inner side of the arm is positionable against the patient, thereby being sufficiently compact to accommodate a confine of an MRI portal.

19. A method of distracting a wrist joint of a patient, the method comprising:

securing a first anchor of a joint distraction device to a hand of the patient distal of the joint, wherein the first anchor securely holds the patient's hand in a fixed position when clamped within the first anchor;

securing a second anchor of the device to a forearm of the patient proximal of the wrist joint, wherein the first and second anchor are connected by a beam extending length-wise therebetween, wherein a cross-bar of the first anchor is securely affixed to the beam at a fixed location on the beam so as to securely hold the patient's hand at the fixed position for MRI imaging of the wrist joint; and adjusting, with an adjuster of the device that is operably coupled to the beam, a distance between the first and second anchor, thereby distracting the wrist joint, wherein the second anchor is disposed entirely on the forearm of the patient such that the arm is positionable straight alongside the patient; and performing imaging and/or arthroscopy of the joint by MRI imaging while the joint distraction device is worn by the patient with the beam disposed on an outer side of the hand and arm such that an inner side of the hand and arm is positioned straight alongside the patient in a supine position while the wrist joint is held in distraction.

20. The method of claim 19, wherein the joint distraction device is configured for distraction of the wrist joint, wherein the first anchor comprises a plurality of finger clamps each attached to the cross-bar at fixed positions so as to secure the hand in the fixed position and the second anchor comprises an arm sleeve that attaches to the forearm.

21. The method of claim 19, wherein adjusting the distance between the first and second anchor comprises extending the beam from one of the first and second anchors.

22. The method of claim 19, wherein adjusting the distance between the first and second anchor comprises adjusting a position of at least one of the first and second anchors on the beam.

23. The method of claim 22, wherein adjusting the distance between the first and second anchor comprises incrementally adjusting the position of the first anchor on a plurality of notches or ridges on a fluted portion of the beam.

24. The method of claim 19, wherein the device is fully wearable and operable without attachment to any external pulley system or external weights.

25. The method of claim 19, wherein the device is fully wearable and operable without being attached to any external device or system.

26. The method of claim 19, wherein the adjuster is manually operated.

27. The method of claim 19, wherein the adjuster is electrically actuated.

28. The method of claim 19, wherein the device extends linearly such that the arm is held straight with both the elbow and wrist joints unbent.

29. The method of claim 19, wherein the device is attached on the outer side of the patient's hand and arm such that the inner side of the arm is positionable against the patient, thereby being sufficiently compact to accommodate a confine of an MRI portal.

* * * * *